United States Patent [19]

Stern

[11] 4,425,363
[45] Jan. 10, 1984

[54] TREATMENT OF TARDIVE DYSKINESIA IN MAMMALS

[75] Inventor: Warren C. Stern, Raleigh, N.C.

[73] Assignee: Burroughs Wellcome Co., Research Triangle Park, N.C.

[21] Appl. No.: 395,118

[22] Filed: Jul. 6, 1982

Related U.S. Application Data

[63] Continuation of Ser. No. 263,718, May 14, 1981, abandoned.

[51] Int. Cl.³ ............................................ A61K 31/135
[52] U.S. Cl. ..................................................... 424/330
[58] Field of Search ........................................ 424/330

[56] References Cited

U.S. PATENT DOCUMENTS 3,819,706  6/1974  Mehta ................................. 424/330
3,885,046  5/1975  Mehta ................................. 424/330

OTHER PUBLICATIONS

Ferris et al., Studies Concerning the Mechanism of The/Antidepressant Activity of Bupropion, J. Clin. Psychiatry, (1982).
Laakmann et al., Life Sciences, vol. 30, pp. 1725–1732, (1982), Pergamon Press.
Butz et al., Inpress: Jour. Exp. Pharmacology of Therapeutics, (1982), The Relationship Between Bupropion Disposition & Dopamine Uptake in Rats and Mice.
Ferris et al., Typical & Atypical Antidepressants, Molecular Mechanisms, Raven Press, New York, (1982), pp. 277–286.
Ferris et al., Drug Development Research 1: 21–35, (1981).
Soroko et al., Communications, J. Pharm. Pharmac., (1977), 29, 767–770.
Canning et al., Brit. Jour. of Pharmacology, (1979): 66 104–105.
Whiteman et al., Jour. of Clin. Psychiatry, (1982), Failure of Bupropion to Affect Prolacter or Growth Hormone.
Pharmacological and Biochemical Properties of Drug Substances, vol. 3, "Bupropion", Maxwell et al., Amer. Pharm. Ass. Academy of Pharm. Sciences Publish.

Primary Examiner—Stanley J. Friedman
Attorney, Agent, or Firm—Robert T. Gammons

[57] ABSTRACT

A method of Treatment of Tardive Dyskinesia (TD) in humans by the administration of the compound of the formula

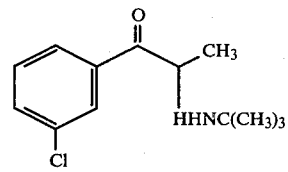

or a pharmaceutically acceptable acid addition salt thereof in a non-toxic, effective therapeutic amount (calculated as base) to a human in need thereof.

10 Claims, No Drawings

TREATMENT OF TARDIVE DYSKINESIA IN MAMMALS

This is a continuation of application Ser. No. 263,718 filed May 14, 1981, now abandoned.

BACKGROUND OF THE INVENTION

This invention is directed to a method of Treatment of Tardive Dyskinesia (TD) in humans having Tardive Dyskinesia by the administration of the humans of the compound of the formula I

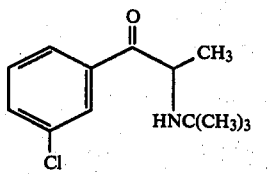

or a pharmaceutically acceptable acid addition salt thereof in a non-toxic, therapeutic amount (calculated as base) to a human in need thereof.

In U.S. Pat. Nos. 3,819,706 and 3,885,046, the compound of formula I (named m-chloro-α-t-butylaminopropiophenone) and salts thereof were disclosed as being antidepressants. It has now been found that the compound of formula I and its pharmaceutically acceptable salts thereof will effectively treat TD in humans.

TD is a frequently irreversible motor disorder occurring following long-term treatment of humans with neuroleptic drugs. At present, there is no FDA approved pharmacological treatment for TD.

The symptoms of TD most commonly consist of uncontrollable rhythmic movements of the tongue, mouth, facial and neck muscles, and may involve the entire upper body musculature.

See the Text The Basal Ganglia vol. 55, RAVEN PRESS © 1976 P427 to 432 for a description of Tardive Dyskinesia: Manifestations, Medical, Etiology and Treatment.

The compounds of formula (I) (the active ingredient) or the pharmaceutically acceptable acid addition salt thereof is preferably administered in unit dosage form to the human having (suffering) from Tardive Dyskinesia.

The compound or salt of this invention may be administered orally, parenterally or rectally.

A pharmaceutical composition containing a compound of formula (I), or a pharmaceutically acceptable acid addition salt thereof, may be presented in discrete units such as tablets, capsules, ampules or suppositories, each containing an effective amount of the compound or salt for treatment of Tardive Dyskinesia.

As an example, for the treatment of humans having Tardive Dyskinesia the preferred unit dosage of a compound of formula (I) or an acid addition salt thereof (estimated as the base) for oral administration, or administration as a suppositiory, is about 15 milligrams to 500 milligrams, preferably 15 milligrams to 300 milligrams, and the most preferred unit dosage being 150 milligrams to 250 milligrams per day, three times daily, for a 70 kg adult. Treatment is to be given continuously for months or years as determined by the physician. The effective (therapeutic) dosage in humans for the treatment of Tardive Dyskinesia is preferably 1 to 10 mg/kg orally per day (calculated as base). Parenteral administrations may be used and in this case the parenteral dose would be about ½ the oral dosage. All the above doses are given in terms of the weight of a compound of formula (I) in the form of its base, but as will be appreciated from the foregoing information, it may be administered in the form of a pharmaceutically acceptable acid salt thereof.

A compound of formula (I) or pharmaceutically acceptable acid addition salt thereof may be presented as an oral unit preparation (for example as a cachet, tablet or capsule) containing one or more pharmaceutically acceptable carriers which may take the form of solid diluents such as lactose, cornstarch, micronized silica gel as well as other excipients known in the art.

It should be understood that in addition to the aforementioned incredients, the pharmaceutical compositions of this invention may include one or more of additional ingredients such as diluents, buffers, flavouring agents, binders, surface active agents, thickeners, lubricants, preservatives, and the like. The formulations may be prepared by admixture of the ingredients, and, if necessary, shaping the resulting mass, and filling into suitable containers.

The compound used in this invention is preferably presented for use as a pharmaceutically acceptable salt. Examples of suitable salts include the hydrochloride, sulfuric, phosphoric, and toluenesulphonic.

Reference should be had to U.S. Pat. Nos. 3,819,706 and 3,885,046, which are incorporated herein by reference hereto for a discription of the preparation of the compound of formula (I), salts thereof, tablets, capsules, parenteral solutions and suppositories incorporating same.

EXAMPLE I

The hydrochloride salt of formula I is administered as a tablet to a human (man) who has been identified by a clinician as having the symptoms associated with tardive dyskinesia. The man (70 kg) is orally administered a daily dose of 6 mg/kg (calculated as base) in three equally divided doses 6 hours between doses.

The man is treated continuously for the symptoms. 420 mg is administered to 70 kg man daily.

EXAMPLE II

The procedure of Example I is followed however the hydrochloride salt at the same dosage is orally administered as a cherry flavored aqueous solution, 1 teaspoon three times daily (130 mg base per spoonful).

We claim:

1. A method of treating Tardive Dyskinesia in a human having Tardive Dyskinesia which comprises administering to said human an effective non-toxic Tardive Dyskinesia amount of a compound of the formula (I)

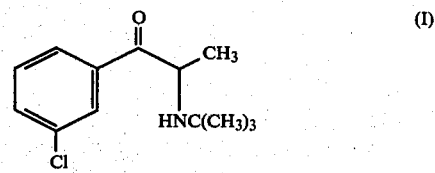

or a pharmaceutically acceptable and acid addition salt thereof.

2. The method of claim 1 in which a pharmaceutically acceptable salt thereof is administered.

3. The method of claim 2 in which the salt is the hydrochloride salt.

4. The method of claim 1, 2, or 3 in which the compound or salt is administered in a pharmaceutically acceptable carrier therefore.

5. The method of claim 4 in which the compound or salt is administered orally.

6. The method of claim 4 in which the compound or salt is administered parenterally.

7. A method of treating Tardive Dyskinesia in a human having Tardive Dyskinesia which comprises orally administering to said human an effective acid addition Tardive Dyskinesia treatment amount of a pharmaceutically acceptable acid addition salt of the compound of the formula (I)

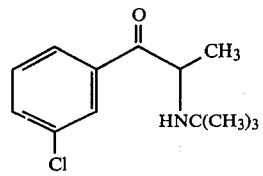

8. The method of claim 7 in which the salt is the hydrochloric salt.

9. The method of claim 7 or 8 in which the salt is administered in a pharmaceutically acceptable carrier therefor in the form of a tablet or capsule.

10. A method of treating Tardive Dyskinesia in a human having Tardive Dyskinesia which comprises parenterally administering to said human an effective non-toxic Tardive Dyskinesia treatment amount of a parenteral composition containing a pharmaceutically acceptable acid addition salt of the compound of the formula (I)

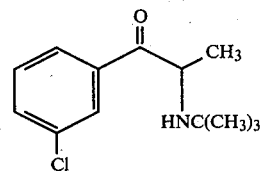

* * * * *